US012669499B2

(12) United States Patent
Cheng et al.

(10) Patent No.: US 12,669,499 B2
(45) Date of Patent: Jun. 30, 2026

(54) PROBES COMPRISING METAL NANOPARTICLES, MAGNETIC NANOPARTICLES AND TARGET-SPECIFIC FLUOROPHORES OR BINDING SITES

(71) Applicant: Oregon State University, Corvallis, OR (US)

(72) Inventors: Li-Jing Cheng, Corvallis, OR (US); Ye Liu, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 1141 days.

(21) Appl. No.: 17/697,638

(22) Filed: Mar. 17, 2022

(65) Prior Publication Data

US 2022/0308047 A1 Sep. 29, 2022

Related U.S. Application Data

(60) Provisional application No. 63/165,953, filed on Mar. 25, 2021.

(51) Int. Cl.
| | |
|---|---|
| *C12Q 1/6825* | (2018.01) |
| *C12Q 1/6834* | (2018.01) |
| *G01N 21/64* | (2006.01) |
| *G01N 21/65* | (2006.01) |
| *G01N 33/543* | (2006.01) |

(52) U.S. Cl.
CPC ....... *G01N 33/5434* (2013.01); *C12Q 1/6825* (2013.01); *C12Q 1/6834* (2013.01); *G01N 21/6428* (2013.01); *G01N 21/658* (2013.01); *G01N 33/54333* (2013.01); *G01N 33/54393* (2013.01); *G01N 2021/6439* (2013.01); *G01N 2446/20* (2013.01)

(58) Field of Classification Search
None
See application file for complete search history.

(56) References Cited

PUBLICATIONS

Wu et al., Small, 2020, 16, 1905734: 1-7. (Year: 2020).*
Chen et al., "Highly sensitive and selective detection of nitrite ions using Fe$_3$O$_4$@SiO$_2$/Au magnetic nanoparticles by surface-enhanced Raman spectroscopy," *Biosensors and Bioelectronics* 85:726-733, 2016.

Kanwal et al., "Synthesis and characterization of silver nanoparticle-decorated cobalt nanocomposites (Co@AgNPs) and their density-dependent antibacterial activity," *Royal Society Open Science* 6:182135, 2019.
Levin et al., "Magnetic-Plasmonic Core-Shell Nanoparticles," *ACS Nano* 3(6):1379-1388, 2009.
Ramalingam et al., "Facile Synthesis of Silver Nanoparticles Decorated Magnetic-Chitosan Microsphere for Efficient Removal of Dyes and Microbial Contaminants," *ACS Sustainable Chemistry & Engineering* 3:2291-2302, 2015.
Ramalingam et al., "Supporting Information—Facile Synthesis of Silver Nanoparticles Decorated Magnetic-Chitosan Microsphere for Efficient Removal of Dyes and Microbial Contaminants—Supporting Information," *ACS Sustainable Chemistry & Engineering* 3:2291-2302, 2015.
Sangili et al., "Synthesis of silver nanoparticles decorated on core-shell structured tannic acid-coated iron oxide nanospheres for excellent electrochemical detection and efficient catalytic reduction of hazardous 4-nitrophenol," *Composites Part B: Engineering*, 162:33-42, 2019.
Silva et al., "Gold coated magnetic nanoparticles: from preparation to surface modification for analytical and biomedical applications," *Chemical Communications* 52:7528-7540, 2016.
Wang et al., "Seed-mediated synthesis of high-performance silver-coated magnetic nanoparticles and their use as effective SERS substrates, Colloids and Surfaces," *A: Physicochemical and Engineering Aspects* 506:393-401, 2016.
Xu et al., "Magnetic Core/Shell Fe3O4/Au and Fe3O4/Au/Ag Nanoparticles with Tunable Plasmonic Properties," *Journal of the American Chemical Society* 129:8698-8699, 2007.

* cited by examiner

*Primary Examiner* — Nicole Kinsey White
(74) *Attorney, Agent, or Firm* — Klarquist Sparkman, LLP

(57) ABSTRACT

Disclosed probes comprise metal nanoparticle cores associated with magnetic particles that allow probes associated with targets to be concentrated by an applied magnetic field to increase detection sensitivity and provide sufficient spacing between concentrated probes to avoid signal quenching. The probe may comprise at least one recognition receptor, and may further comprise at least one reporter molecule, such as a fluorescent tag, a Raman reporter, or combinations thereof. Concentrating probe-target composites substantially enhances a sensing signal, such as from 5 to 10 times, compared to detection without concentrating the probes. The method may be used to detect, for example, interleukins at concentrations at least as low as 25 pg/ml in sputum or blood from a subject for early and precise profiling of viral infections, such as SARS-CoV-2 infections.

22 Claims, 7 Drawing Sheets

Specification includes a Sequence Listing.

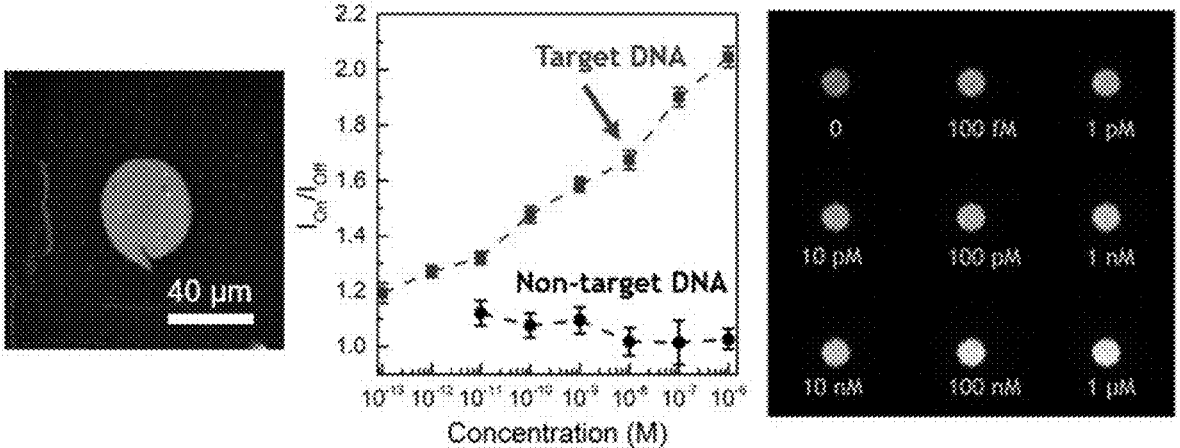
FIG. 5A                    FIG. 5B                    FIG. 5C
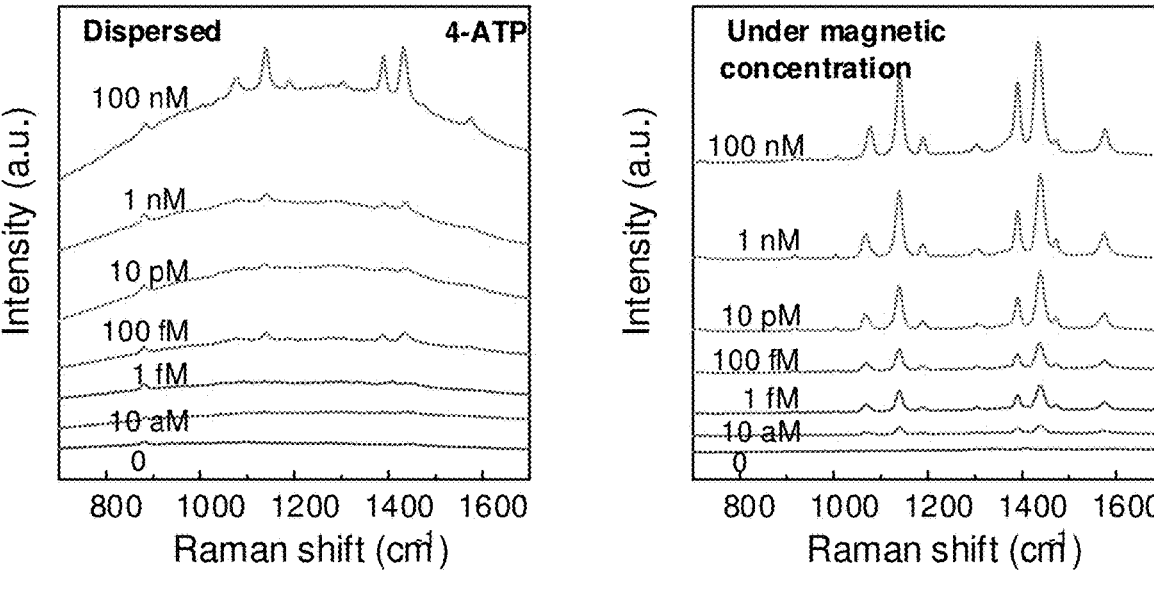
FIG. 6A                              FIG. 6B

SEQUENCE LISTING

```
<160> NUMBER OF SEQ ID NOS: 3

<210> SEQ ID NO 1
<211> LENGTH: 32
<212> TYPE: DNA
<213> ORGANISM: Artificial Sequence
<220> FEATURE:
<223> OTHER INFORMATION: Flourescent dye labeled nucleic acid probe
<220> FEATURE:
<221> NAME/KEY: misc_feature
<222> LOCATION: (32)..(32)
<223> OTHER INFORMATION: dye functionalized base

<400> SEQUENCE: 1
gcgcgtcaac atcagtctga taagctacgc gc                                    32

<210> SEQ ID NO 2
<211> LENGTH: 22
<212> TYPE: DNA
<213> ORGANISM: Artificial Sequence
<220> FEATURE:
<223> OTHER INFORMATION: Target nucleic acid

<400> SEQUENCE: 2
tagcttatca gactgatgtt ga                                               22

<210> SEQ ID NO 3
<211> LENGTH: 23
<212> TYPE: DNA
<213> ORGANISM: Artificial Sequence
<220> FEATURE:
<223> OTHER INFORMATION: Non-target control
```

<400> SEQUENCE: 3
ttaatgctaa tcgtgatagg ggt            23

PROBES COMPRISING METAL NANOPARTICLES, MAGNETIC NANOPARTICLES AND TARGET-SPECIFIC FLUOROPHORES OR BINDING SITES

CROSS REFERENCE TO RELATED APPLICATION

This application claims the benefit under 35 U.S.C. § 119(e) of the Mar. 25, 2021 earlier filing date of U.S. provisional patent application No. 63/165,953. U.S. provisional patent application No. 63/165,953 is incorporated herein by reference in its entirety.

ACKNOWLEDGMENT OF GOVERNMENT SUPPORT

This invention was made with government support under Award No. ECCS 1810067 awarded by the National Science Foundation. The United States government has certain rights in the invention.

INCORPORATION OF ELECTRONIC SEQUENCE LISTING

The electronic sequence listing, submitted herewith as ASCII text file named Sequence Listing.txt, 1,032 bytes, created on Sep. 24, 2025, is herein incorporated by reference in its entirety.

FIELD

The present disclosure concerns analytical probes, particularly molecular probes, and even more particularly biosensor probes comprising target-specific metal nanoparticle cores associated with magnetic particles and further comprising reporter molecules, such as fluorescent tags and/or Raman reporters.

BACKGROUND

Detection of fluorescence or Raman signals is a common and well-known experimental procedure to detect target molecules at very low concentration. Traditional probe structures may have multiple metal nanoparticles or fluorescence probes conjugated around a magnetic particle to facilitate manipulating the probes. However, the fluorescent dyes in these structures are located at the outermost surface or periphery of the probe. Such a configuration is problematic because once the probes are concentrated in proximity, the fluorescence signal may be quenched by neighboring probes, reducing the signal and as a result the sensitivity of the detection method. Therefore, there remains a need in the art for new technology that addresses the deleterious issues associated with these prior approaches.

SUMMARY

Certain disclosed embodiments provide probes comprising metal nanoparticle cores that are associated with magnetic particles. The magnetic particles allow probes associated with targets to be concentrated, thereby substantially increasing the detection sensitivity, while at the same time providing sufficient spacing between concentrated probes to avoid signal quenching.

One disclosed embodiment of a biosensor probe comprises a core comprising a metal nanoparticle having a metal nanoparticle surface, and at least one, and typically plural, magnetic nanoparticle associated with the core. The metal nanoparticle typically comprises a metal selected from gold, silver, copper, aluminum, alloys thereof, and combinations thereof, and the magnetic nanoparticle typically comprises iron, iron oxide, nickel, cobalt, or combinations thereof. For embodiments comprising plural magnetic nanoparticles, such nanoparticles typically cover greater than 0 to less than about 50% of the metal nanoparticle core surface, such as from 10% to 30% of the metal nanoparticle core surface. The probe may comprise at least one recognition receptor, and potentially plural recognition receptors, associated with the metal nanoparticle for recognizing a selected target. Exemplary recognition receptors include peptides, proteins, such as an antibody, nucleic acids, such as single or double stranded oligonucleotides, molecularly imprinted polymers, or combinations thereof. The probe may comprise at least one reporter molecule, and potentially plural reporter molecules, such as a fluorescent tag, a Raman reporter, or combinations thereof. The metal nanoparticle size may be selected to create a plasmon resonance spectrum that matches the light excitation or a dye emission wavelength to enhance the fluorescence or Raman signal.

Embodiments of a method for using such probes also are disclosed. For example, the method may comprise providing an embodiment of a probe according to the present invention, and contacting a sample potentially comprising a target of interest with the probe to form a probe-target composite. Probe-target composites are concentrated using an applied magnetic field to form concentrated probe-target composites, and the concentrated probe-target composites are then detected, such as by detecting a fluorescent signal, obtaining a Raman spectrum, or both. Concentrating the probe-target composites substantially enhances a sensing signal, such as from 5 to 10 times, compared to detection without concentrating the probes. The probe-target composites often are concentrated on a surface, such as a glass surface, which may include an anti-fouling treatment, such as a surface treated with bovine serum albumin, casein, an alkylene glycol, such as polyethylene glycol, zwitterionic molecules, or combinations thereof.

A person of ordinary skill in the art will appreciate that a number of targets can be detected using such method. For example, the target might be a virus, such as SARS-COV-2 or a mutant strain thereof. The sample may be a biological fluid, such as sputum or blood. The method may be used to detect interleukins, including by way of example interleukin-6 (IL-6), interleukin-2 (IL-2), and interleukin-1β (IL-1β), or combinations thereof, at concentrations at least as low as 25 pg/ml. The interleukins may be detected in sputum or blood from a subject for early and precise profiling of SARS-COV-2 infections.

The foregoing and other objects, features, and advantages of the invention will become more apparent from the following detailed description, which proceeds with reference to the accompanying figures.

BRIEF DESCRIPTION OF THE DRAWINGS

FIG. 5A is a fluorescence image of one embodiment of a biosensor probe according to the present invention concentrated by an applied magnetic field.

FIG. 5B is a graph of fluorescence intensities versus concentration (M) for an embodiment of a concentrated biosensor probe according to the present invention associated with target DNA at various concentrations in a sample comprising both target and non-target nucleic acid.

FIG. 5C provides fluorescence images of one embodiment of a concentrated biosensor probe according to the present invention associated with target DNA of different concentrations illustrating probe sensitivity.

FIG. 6A provides Raman spectra [Intensity (a.u.) versus Raman shift (cm$^{-1}$)] of p-aminothiophenol (4-ATP) attached to one embodiment of a silver nanoparticle associated with magnetic nanoparticles to form dispersed composites with the plasmonic resonance wavelength of the silver particle at 480 nm.

FIG. 6B provides Raman spectra [Intensity (a.u.) versus Raman shift (cm$^{-1}$)] of p-aminothiophenol (4-ATP) attached to one embodiment of a silver nanoparticle associated with magnetic nanoparticles and concentrated under an applied magnetic field to form concentrated composites with the plasmonic resonance wavelength of the silver particle at 480 nm illustrating the substantially increased sensitivity obtained using concentrated probe embodiments of the present invention.

SEQUENCE LISTING

Figure 1:
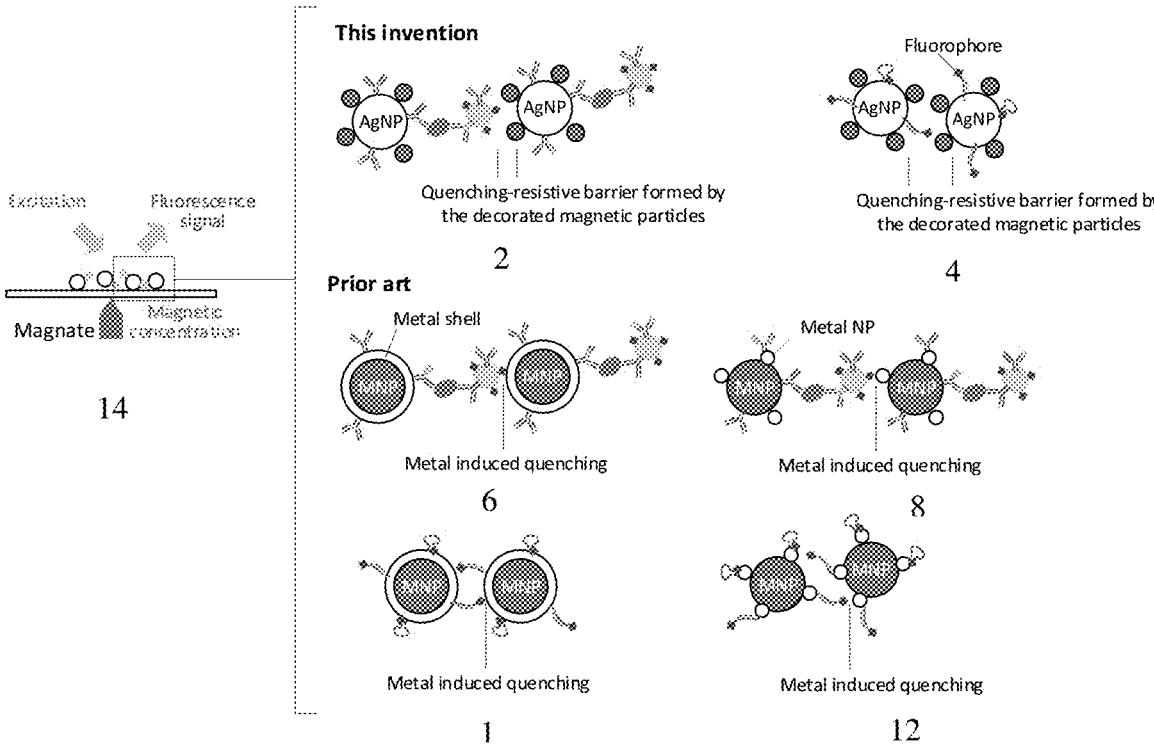
FIG. 1 is a schematic drawing illustrating one embodiment of a composition (top) according to the present invention comprising metal nanoparticle-magnetic nanoparticle probes associated with a target and a reporter compared to other compositions (middle and bottom) known in the art.

The nucleic acid sequences listed in the accompanying sequence listing are shown using standard letter abbreviations for nucleotide bases as defined in 37 C.F.R. § 1.822. Only one strand of each nucleic acid sequence is shown, but the complementary strand is understood as included by any reference to the displayed strand.

SEQ ID NO: 1 is a nucleic acid sequence of a fluorescent dye-labeled nucleic acid probe.

SEQ ID NO: 2 is a nucleic acid sequence of a target nucleic acid sequence.

SEQ ID NO: 3 is a nucleic acid sequence of a non-target nucleic acid sequence.

DETAILED DESCRIPTION

I. Terms and Definitions

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

The disclosure of numerical ranges should be understood as referring to each discrete point within the range, inclusive of endpoints, unless otherwise noted. Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Antibody: "Antibody" collectively refers to immunoglobulins or immunoglobulin-like molecules [including by way of example and without limitation, IgA, IgD, IgE, IgG and IgM, combinations thereof, and similar molecules produced during an immune response in any chordate such as a vertebrate, for example, in mammals such as humans, goats, rabbits and mice] and fragments thereof that specifically bind to a molecule of interest (or a group of highly similar molecules of interest) to the substantial exclusion of binding to other molecules. An "antibody" typically comprises a polypeptide ligand having at least a light chain or heavy chain immunoglobulin variable region that specifically recognizes and binds an epitope of an antigen. Immunoglobulins are composed of a heavy and a light chain, each of which has a variable region, termed the variable heavy ($V_H$) region and the variable light ($V_L$) region. Together, the $V_H$ region and the $V_L$ region are responsible for binding the antigen recognized by the immunoglobulin. Exemplary immunoglobulin fragments include, without limitation, proteolytic immunoglobulin fragments [such as F(ab')$_2$ fragments, Fab' fragments, Fab'-SH fragments and Fab fragments as are known in the art], recombinant immunoglobulin fragments (such as sFv fragments, dsFv fragments, bispecific sFv fragments, bispecific dsFv fragments, F(ab)'$_2$ fragments, single chain Fv proteins ("scFv"), and disulfide stabilized Fv proteins ("dsFv"). Other examples of antibodies include diabodies, and triabodies (as are known in the art), and camelid antibodies. "Antibody" also includes genetically engineered molecules, such as chimeric antibodies (for example, humanized murine antibodies), and heteroconjugate antibodies (such as, bispecific antibodies). See also, *Pierce Catalog and Handbook,* 1994-1995 (Pierce Chemical Co., Rockford, IL); Kuby, J., *Immunology,* 3$^{rd}$ Ed., W.H. Freeman & Co., New York, 1997.

Conjugate: Two or more moieties directly or indirectly coupled together. For example, a first moiety may be covalently or noncovalently (e.g., electrostatically) coupled to a second moiety. Indirect attachment is possible, such as by using a "linker" (a molecule or group of atoms positioned between two moieties).

Conjugating, joining, bonding or linking: Coupling a first unit to a second unit. This includes, but is not limited to, covalently bonding one molecule to another molecule, non-covalently bonding one molecule to another (e.g. electrostatically bonding) (see, for example, U.S. Pat. No. 6,921,496, which discloses methods for electrostatic conjugation), non-covalently bonding one molecule to another molecule by hydrogen bonding, non-covalently bonding one molecule to another molecule by van der Waals forces, and any and all combinations of such couplings.

Coupled: The term "coupled" means joined together, either directly or indirectly. A first atom or molecule can be directly coupled or indirectly coupled to a second atom or molecule. A secondary antibody provides an example of indirect coupling. One specific example of indirect coupling is a rabbit anti-hapten primary antibody that is bound by a mouse anti-rabbit IgG antibody, which is in turn bound by a goat anti-mouse IgG antibody that is covalently linked to a detectable label.

Detect: To determine if an agent (such as a signal or particular antigen, protein or nucleic acid) is present or absent, for example, in a sample. In some examples, this can further include quantification, and/or localization, for example localization within a cell or particular cellular compartment. "Detecting" refers to any method of determining if something exists, or does not exist, such as determining if a target molecule is present in a biological sample. For example, "detecting" can include using a visual or a mechanical device to determine if a sample displays a specific characteristic. In certain examples, detection refers to visually observing a probe bound to a target or observing that a probe does not bind to a target.

Detectable Label: A molecule or material that can produce a detectable (such as visually, electronically or otherwise) signal that indicates the presence and/or concentration of a target, such as a target molecule, in a sample, such as a tissue sample. When conjugated to a specific binding molecule, the detectable label can be used to locate and/or quantify the target to which the specific binding molecule is directed. Thereby, the presence and/or concentration of the target in a sample can be detected by detecting the signal produced by the detectable label. A detectable label can be detected directly or indirectly, and several different detectable labels conjugated to different specific-binding molecules can be used in combination to detect one or more targets. For example, a first detectable label, such as a hapten conjugated to an antibody specific to a target, can be detected indirectly by using a second detectable label that is conjugated to a molecule that specifically binds the first detectable label. Multiple detectable labels that can be separately detected can be conjugated to different specific binding molecules that specifically bind different targets to provide a multiplexed assay that can provide detection of the multiple targets in a sample.

Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected through antibody-hapten binding interactions using additional detectably labeled antibody conjugates, paramagnetic and magnetic molecules or materials, Raman reporters, and combinations thereof.

Fluorescence: The emission of visible radiation by an atom or molecule passing from a higher to a lower electronic state, wherein the time interval between absorption and emission of energy is 108 to 103 second. Fluorescence occurs when the atom or molecule absorbs energy from an excitation source (e.g., an ultraviolet lamp) and then emits the energy as visible radiation.

Guest molecule or template molecule: A molecule used as a template in the preparation of a molecularly imprinted polymer. The guest molecule is subsequently removed, leaving a molecular imprint in the polymer.

Hapten: A molecule, typically a small molecule that can combine specifically with an antibody, but typically is substantially incapable of being immunogenic except in combination with a carrier molecule. Examples of haptens include, but are not limited to, fluorescein, biotin, nitroaryls, including, but, not limited to, dinitrophenol (DNP), digoxigenin, oxazole, pyrazole, thiazole, benzofuran, triterpene, urea, thiourea, rotenoid, coumarin and cyclolignan.

Magnetic: Exhibiting magnetism, e.g., attracted by magnetic fields.

Magnetic nanoparticle or MNP(s): Includes all magnetic nanoparticles, including both ferromagnetic and paramagnetic nanoparticles. Accordingly, in some disclosed embodiments, the MNPs are ferromagnetic. In other disclosed embodiments, the MNPs are paramagnetic. In yet further embodiments, the MNPs may comprise a mixture or combination of both paramagnetic and ferromagnetic MNPs.

Molecularly imprinted polymer (MIP): A polymer, such as a crosslinked polymer, synthesized from monomers and a template or guest molecule, followed by removal of the guest molecule, leaving a polymer having imprints or cavities corresponding to the shape of the guest molecule. The imprints or cavities have an affinity for the guest molecule or other molecules with similar shape and/or functional group(s).

MNP@NP, e.g. MNP@AgNP: May be used herein and in the accompanying figures to refer to a composite probe structure comprising a metal nanoparticle with magnetic nanoparticles associated with its surface.

Nanoparticle: A nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoprisms, nanoropes and quantum dots. A nanoparticle can produce a detectable signal, for example, through absorption and/or emission of photons (including radio frequency and visible photons) and plasmon resonance.

Quenching: A process which decreases the intensity of a given substance, such as the fluorescence intensity.

Specifically binds: A term that refers to the binding of agent that preferentially binds to a defined target (such as an antibody to a specific antigen or a nucleic acid probe to a specific nucleic acid sequence). With respect to an antigen, "specifically binds" refers to the preferential association of an antibody or other ligand, in whole or part, with a specific polypeptide. With respect to a nucleic acid sequence, "specifically binds" refers to the preferential association of a nucleic acid probe, in whole or part, with a specific nucleic acid sequence A specific binding agent or moiety binds substantially only to a defined target. It is recognized that a minor degree of non-specific interaction may occur between a molecule, such as a specific binding agent or moiety, and a non-target polypeptide or non-target nucleic acid sequence. Although a selectively reactive antibody binds an antigen, it can do so with low affinity. Antibody to antigen specific binding typically results in greater than 2-fold, such as greater than 5-fold, greater than 10-fold, or greater than 100-fold increase in amount of bound antibody or other ligand (per unit time) to a target polypeptide, as compared to a non-target polypeptide. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, Antibodies, A Laboratory Manual, Cold Spring Harbor Publications, New York (1988), for a description of immunoassay formats and conditions that can be used to determine specific immunoreactivity.

II. Disclosed Embodiments

A. Features of Particular Embodiments

Certain disclosed embodiments include one or more of the following features:

1. Magnetic particle-decorated metal nanoparticles yield a stronger plasmonic resonance for fluorescence or Raman signal enhancement. The metal shell-magnetic core particles, as are known in the art, by contrast provide a poor plasmonic resonance and thus less signal enhancement.

2. Detection is performed under an applied magnetic field to achieve magnetic concentration for signal enhancement.

3. When the particles are concentrated for detection, the magnetic particles decorated around a metal surface form a physical spacer that prevents fluorescence quenching due to the direct contact between the fluorophore and the metal surface of the neighboring particle.

4. For immunodetection, when the target is captured by a magnetic particle-decorated metal particle and labeled by the reporter particle, the fluorophore or Raman reporter is situated between two metal particles, which provides a strong signal enhancement.

B. Schematic Representation of Composite Structure

FIG. 1 provides a schematic representation of one disclosed embodiment (top) of the present technology compared to other compositions and methods for using such compositions as are known in the art (shown middle and bottom). With reference to a top portion of FIG. 1, a composite structure 2 or 4, also referred to herein as a biosensor probe, according to the present invention comprises a metal nanoparticle, exemplified in FIG. 1 by silver nanoparticles, having magnetic nanoparticles associated with the surface thereof. FIG. 1 also illustrates that the metal nanoparticle-magnetic nanoparticle composites 2 or 4 include target recognition moieties, such as antibodies, that recognize and associate with a particular target. The metal nanoparticle-magnetic nanoparticle composites 2 and 4 also include a reporter that allows the metal nanoparticle-magnetic nanoparticle composites to be detected once associated with a target, such as a Raman reporter (2) or a fluorophore (4). The magnetic particles on the external surface of the metal nanoparticles provide a physical spacer for the biorecognition receptors and fluorescence dyes to avoid fluorescence quenching when the probes are brought together in close proximity by magnetic field for signal enhancement. That is, the magnetic particles form a quenching resistive barrier that spaces metal nanoparticle-magnetic nanoparticle composite structures one from another sufficiently to substantially reduce or eliminate quenching that has been observed, and that limits the effectiveness, of prior approaches, as are illustrated in a middle and bottom portion of FIG. 1. Specifically, a middle and bottom portion of FIG. 1 illustrates prior art approaches whereby the magnetic nanoparticle forms a core portion of a magnetic nanoparticle-metal nanoparticle construct, with the magnetic nanoparticle core portion surrounded by a metal nanoparticle shell. In these prior art systems, the metal nanoparticle shell of a first composite is not effectively shielded from the metal nanoparticle shell of a second composite, which results in signal quenching. FIG. 1 also illustrates at 14 that metal nanoparticle-magnetic nanoparticle composites having target molecules and reporter molecules associated therewith may be concentrated by applying a magnetic field, which substantially increases the sensitivity of the composites.

Figure 2:
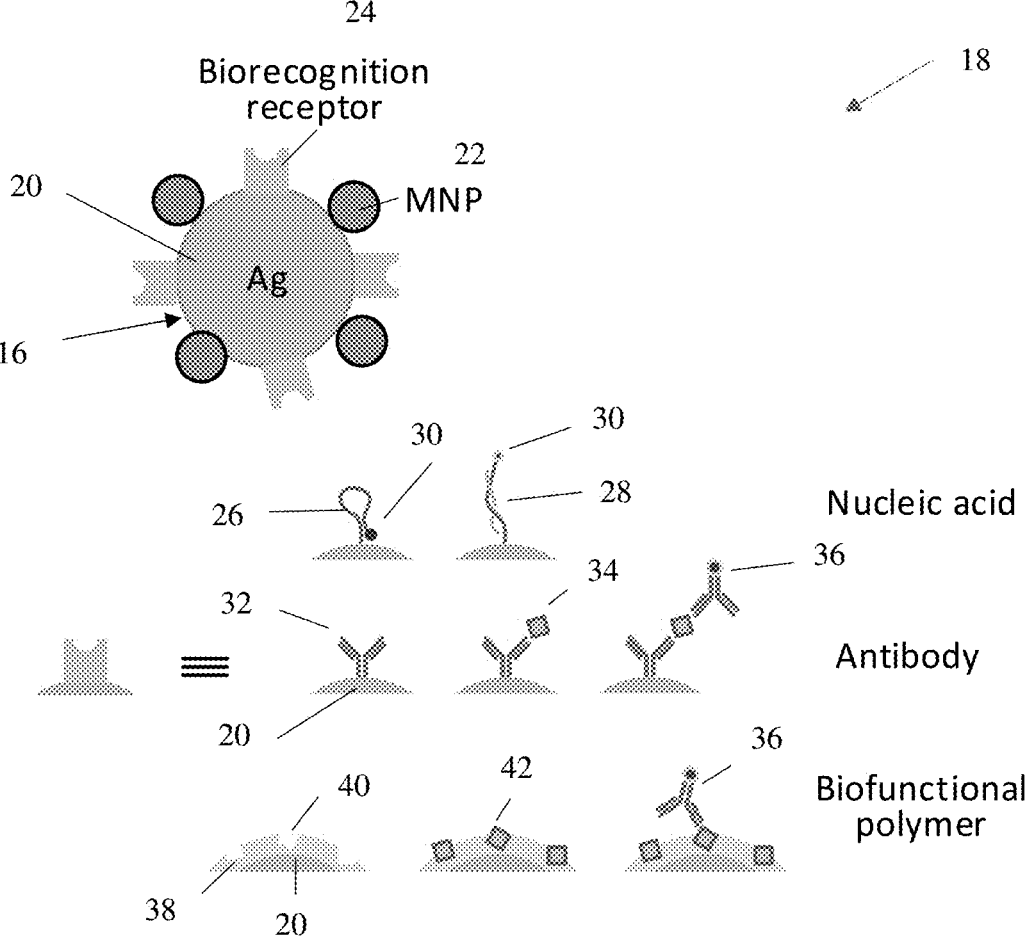
FIG. 2 is a schematic drawing illustrating a biosensor probe comprising an exemplary silver nanoparticle core having magnetic nanoparticles (MNP) associated with a surface thereof, referred to as MNP-decorated silver nanoparticles, which allows the MNPs to serve as a physical spacer for the biorecognition receptors and fluorescence dyes to avoid fluorescence quenching when the probes are concentrated by an applied magnetic field for signal enhancement, together with a TEM image of a biosensor probe according to the invention.

FIG. 2 schematically illustrates a composite structure 16 according to the present disclosure adjacent a TEM image 18 of an actual composite made according to the present invention. Composite structure 16 includes a core nanoparticle 20, such as a silver nanoparticle, at least one, and typically plural magnetic nanoparticles 22, and at least one, and typically plural, biorecognition receptors 24 associated with the metal nanoparticle core. Biorecognition receptors 24 may be associated with the metal nanoparticle surface, as opposed to the MNP. A person of ordinary skill in the art will appreciate that any of a number of biorecognition receptors 24 may be used, either alone or in combination, to form suitable composites according to the present disclosure. For example, and without limitation, the biorecognition receptor may comprise a nucleic acid, either a single stranded nucleic acid 26, or a double stranded nucleic acid 28. The nucleic acid can include a reporter 30, such as a fluorescent tag or Raman reporter, to allow detection once composite 16 binds to a desired biomolecule.

The biorecognition receptor 16 also may be a peptide, a protein, or fragment thereof, including an antibody or antibodies. For example, as illustrated by FIG. 2, the biorecognition receptor 16 associated with the metal nanoparticle 20 may be a primary antibody 32 that specifically binds to a specific binding partner 34. Specific binding partner 34 can be any suitable structure, such as a protein or hapten. Specific binding partner 34 is itself recognized by a secondary antibody 36. Secondary antibody 36 includes a reporter

30 that allows detection once the composite binds to a desired target, such as a biomolecule.

The biorecognition receptor 16 may also comprise a polymer, such as a biofunctional polymer 38, associated with the metal nanoparticle 20. Biofunctional polymer 38 is synthesized to include a pocket 40 that is sized and shaped to receive a specific target molecule 42. Secondary antibody 36 may include a reporter 30 that allows detection once the biofunctional polymer binds to a desired target, such as a biomolecule. Without the reporter, the target molecule received by the biofunctional polymer can be detected by Raman spectroscopy.

Biorecognition receptors 24 may be associated with the metal nanoparticle 20 by any of a number of different association mechanism or bonds. For example, biorecognition receptors 24 may be associated with the metal nanoparticle covalently, by polar covalent bonds, electrostatically and/or by adsorption.

The binding of target molecules can be directly measured by the fluorescence or Raman signals of the target itself. The binding can also be detected by further labeling the composite with a reporter 30 to produce a fluorescence signal or Raman scattering signal that is altered by the binding of the target molecule. The fluorescence or Raman scattering signal can be enhanced by the metal nanoparticle in the vicinity.

Other embodiments may comprise fluorescently labeled molecular beacons in which the fluorescence dye is quenched by the metal surface in the absence of target molecules and enhanced in the presence of target molecules. The probes are concentrated on a surface under an applied magnetic field for the detection of fluorescence or Raman signals.

The metal nanoparticle can comprise any suitable metal, including gold, silver, copper, aluminum, or their alloys. Silver is commonly used throughout this disclosure to exemplify suitable nanoparticles. The size of the metal nanoparticles is chosen to provide the absorbance wavelength close to the wavelength of the excitation light. Depending on the excitation wavelength for detection, the size of the silver nanoparticle can range from 10 nm to 200 nm.

The magnetic nanoparticle can comprise any suitable ferromagnetic or paramagnet particle. Exemplary magnetic nanoparticles include iron, iron oxide, nickel, cobalt, or a combination thereof.

Figure 3:
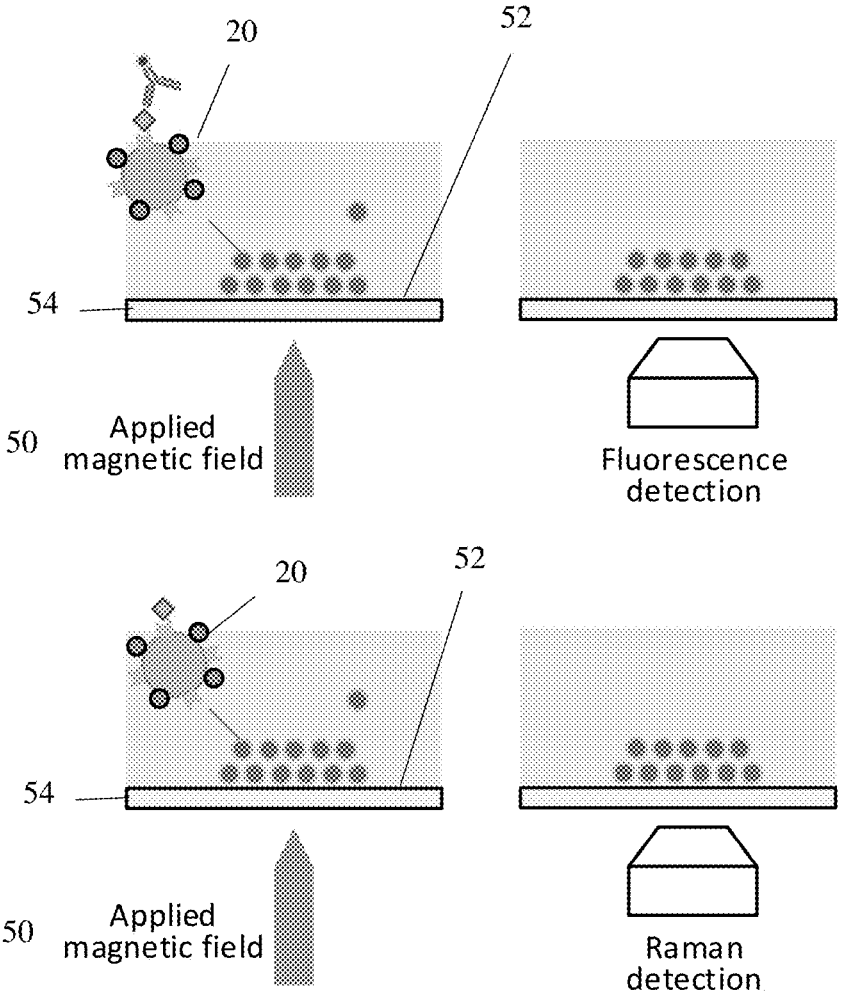
FIG. 3 is a schematic drawing illustrating concentrating probes according to the present invention and detecting a probe signal, such as a fluorescence or Raman signal.

One feature of the present invention is concentration of composite probes to facilitate detection subsequent to binding to a target. This feature is illustrated schematically by FIG. 3. After exposure to a sample, probes associated with a target are concentrated under an applied magnetic field 50 on a surface 52 of a substrate 54 for detection, such as by emitted fluorescence or Raman signals. Concentrating the probes 20 in this manner enhances the sensing signal compared to detection without MNP and an applied magnetic field. For example, concentrating the probes 20 in this manner enhances the sensing signal up to at least 6 times, and potentially as much as 10 times, compared to detection without using MNP and an applied magnetic field. For detection, the biosensor probes 20 are loaded in an enclosed chamber fabricated on a functionalized substrate suitable for magnetic concentration and optical detection. The substrate can be made of any suitable material, such as glass and plastics. Under magnetic concentration, most of the probes are attracted to the substrate surface and migrate on the surface to a concentrated spot. The substrate surface may be treated with an anti-fouling treatment to enhance the mobility of the probes on the surface 52. Without such anti-fouling treatment, the probes 20 tend to stick to the substrate surface 52 over a large area and can hardly be concentrated to a small space, which reduces the signal enhancement. The surface treatment can be any suitable anti-fouling treatment, such as is achieved by coating the surface 52 with bovine serum albumin, casein, an alkylene glycol, such as a poly-alkylene glycol including polyethylene glycol as an example, zwitterionic molecules, such as polymers that contain phosphorylcholine, sulfobetaine and carboxy-betaine, or a combination thereof.

III. Examples

The following examples are provided to illustrate certain particular features of the disclosed embodiments. A person of ordinary skill in the art will appreciate that the invention is not limited to any one of these particular features, nor any such features in combination.

Example 1

This example illustrates an embodiment of a method for making one embodiment of a biosensor probe according to the present invention.

Suitable ferromagnetic nanoparticles were made by providing a mixture of 1,6-hexanediamine (7 grams), anhydrous sodium acetate (2.0 grams) and $FeCl_3 \cdot 6H_2O$ (1.0 gram) in glycol (30 mL). The components of the mixture were dissolved by stirring vigorously at 50° C. This solution was then transferred into a Teflon lined autoclave and reacted at 205° C. for 6 hours.

The MNPs are attached to metal nanoparticles, for example silver nanoparticles, by providing a solution of 10 μl 12 mg/ml magnetic nanoparticles (MNPs) dissolved in 100 μl $AgNO_3$ to achieve a concentration ranging from 2 mM to 20 mM, depending on the size of the silver nanoparticles. A volume ranging from 300 to 900 μl of a 50 mM ascorbic acid was added into the mixture of $AgNO_3$ and MNP solution. 100 μl of a solution mixture comprising 0.1 mM sodium citrate and 10 mM cetrimonium bromide (CTAB) were immediately added for a 10-minute reaction. The CTAB can be replaced by other surfactants, such as triton-X or Tween-20. The size of the silver nanoparticle can be adjusted by controlling the amount of $AgNO_3$. For example, the size of silver nanoparticles made according to this example have ranged from 10 nanometers to a few hundred nanometers. For certain embodiments, the nanoparticle size is selected to create a plasmon resonance spectrum that matches the light excitation or the dye emission wavelength. This spectral overlap is preferred as it enhances the fluorescence or Raman signal of the dye. For certain embodiments, two factors can be varied to reduce or substantially eliminate unwanted scattering or absorption of light contributed by the MNP: size of the nanoparticle; and the percentage of the metal nanoparticle surface that is covered by magnetic particles. MNP of greater than 0 but less than 15 nm diameter have been shown to provide superior results. And covering the surface area of each nanoparticle by greater than 0 to less than 50%, such as from 5% to less than 50%, typically from 10% to 30%, is preferred to eliminate the unwanted scattering or absorption of light contributed by the MNP.

Figure 4A:
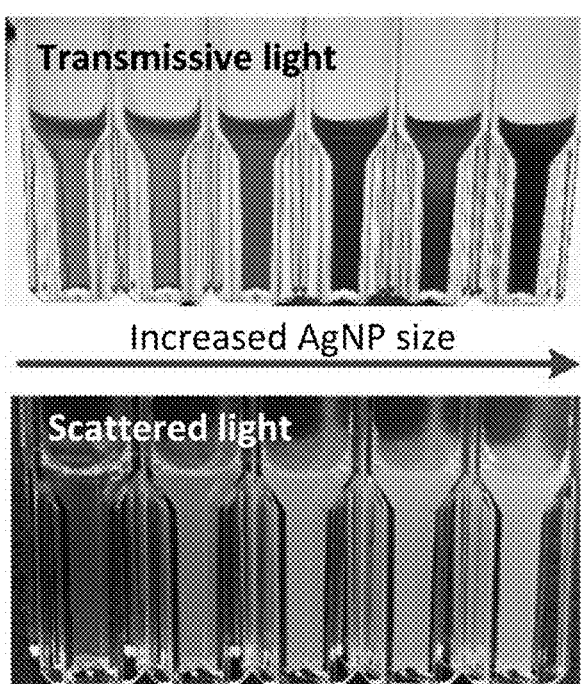
FIG. 4A provides an image of MNP-decorated silver nanoparticle suspensions with various silver nanoparticle (AgNP) sizes that show different colors in transmissive light and scattered light.
Figure 4B:
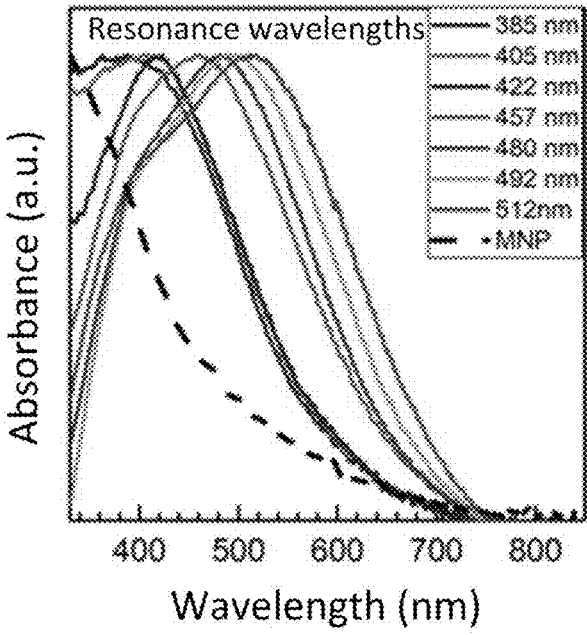
FIG. 4B provides absorbance spectra [absorbance (a.u.) versus wavelength (nm)] of silver core nanoparticles of increasing size having magnetic nanoparticles associated with a surface thereof.

FIG. 4A provides images of MNP-decorated silver nanoparticles of different silver particle sizes ranging from 8 nanometers in diameter to 100 nanometers in diameter dispersed in water. FIG. 4B provides the corresponding absorbance spectra showing that the particle suspensions exhibit surface plasmon resonance wavelengths ranging from 385 nm to 512 nm.

Example 2

This example describes one embodiment of a method for making a substrate for concentrating biosensor probes. For a chamber made on a glass substrate, the glass surface was first cleaned in $H_2O_2$ and $H_2SO_4$ solution (1:3 in volume) for 20 minutes. The glass substrate was then placed in a 1M KOH solution for 20 minutes, followed by sonication in a new 1 M KOH solution. After sonication, the substrate was rinsed in deionized water, followed by rinsing in methanol. The substrate was the immersed in a mixture comprising 100 ml methanol, 5 ml acetic acid, and 150 μl N-(2-aminoethyl)-3-aminopropyltrimethoxysilane (EDA) for 30 minutes. The substrate was then again sonicated and rinsed with methanol. The surface was then contacted with a mixture comprising 8 mg polyethylene glycol (PEG) succinimidyl ester, and 64 μl of a 0.1 M sodium bicarbonate solution at a pH of 8.5. The reaction was allowed to proceed in a dark environment for 2-3 hours to prevent solvent from evaporating. The treated substrate was then rinsed with deionized water and stored in a dark and dry environment at −20° C. until used.

Example 3

This example concerns fluorescence detection of a sequence-selective nucleic acid using a biosensor probe according to the present invention. Synthesized silver nanoparticles with surface-associated magnetic particles were rinsed by solvents, including acetone, ethanol, and deionized water. The nanoparticles were mixed with a DNA probe for 2 hours in 2×PBS buffer. The sensor solution was then washed with 1×PBS buffer with magnetic purification. The resulting biosensor probes were heated to a suitable temperature, e.g., 70° C., for a suitable period of time, such as about 5 minutes, and then cooled at a lower temperature, e.g., 0° C., to form molecular beacon probes.

The biosensor probes were incubated with an analyte solution for hybridization with the target nucleic acid. For this example, the fluorescent dye labeled nucleic acid probe immobilized on the particle had a sequence of 5'-GCGCG TCAAC ATCAG TCTGA TAAGC TACGC GC-dye-3' (SEQ ID NO: 1) that detected a target nucleic acid having a sequence of 5'-TAGCT TATCA GACTG ATGTT GA-3' (SEQ ID NO: 2) in 1×PBS buffer. Nontarget DNA with a sequence of 5'-TTAATGCTAATCGTGATAGGGGT-3' (SEQ ID NO: 3) was used to verify the selectivity. The analyte-probe mixture can be incubated in a separate container for reaction and then loaded into a chamber on a substrate for detection. Alternatively, the incubation and detection can be performed in the same chamber. A magnetic needle was placed near the outer surface of the chamber to attract the biosensor probes on the surface of the chamber. Moving the magnetic needle around the surface of the chamber substrate may facilitate uniform attraction of the probes.

FIG. 5A shows the fluorescence image of the probes concentrated on the chamber substrate under magnetic concentration. FIG. 5B summarizes the fluorescence intensities of the concentrated probes corresponding to the analytes that contain various target and non-target nucleic acid concentrations. The fluorescence images of the sensing results in response to target DNA of different concentrations are presented by FIG. 5C. FIG. 5C establishes that the detection limit for the present example was at least as low as 10 pM.

Example 4

This example concerns enhanced Raman signal detection, where silver nanoparticles associated with magnetic nanoparticles were used to detect target molecules by analyzing their Raman spectra. Target molecules may directly adhere to the surface of the silver particle surface or bind to the silver particle through chemical receptors on the silver surface. After capturing the target molecules, the biosensor probes are concentrated under magnetic force for Raman spectrum measurement. The probes can be concentrated and measured in solution. Alternatively, the concentrated probes can be dried before the measurement.

Figure 6C:
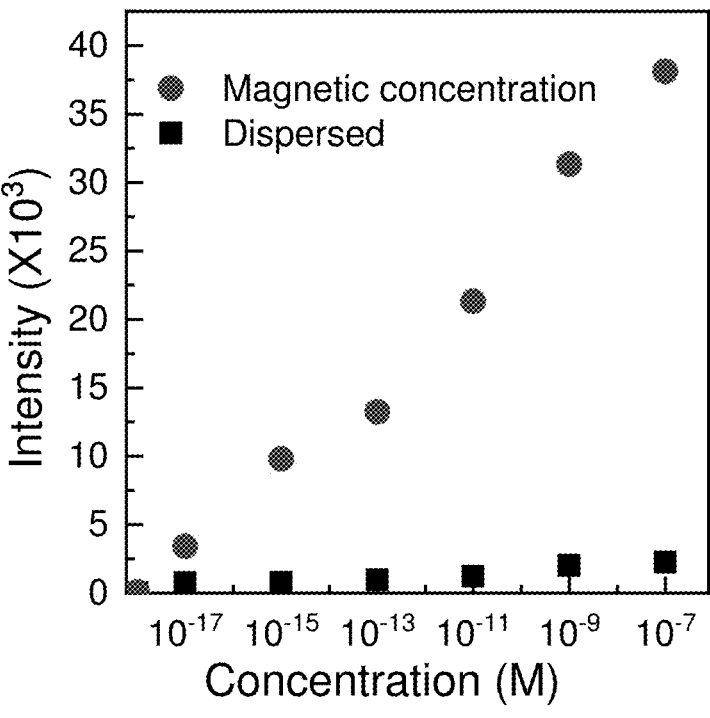
FIG. 6C is a graph of Raman intensity versus 4-ATP concentration (M).

FIG. 6A provides spectra of p-aminothiophenol (4-ATP) of various concentrations immobilized through thiol chemistry on silver nanoparticles associated with magnetic nanoparticle with the plasmonic resonance wavelength of the silver particle at 480 nm. The Raman signals of 4-ATP remains observable at 1 fM from the particles under magnetic concentration, while not much signal is detectable from the particles dispersed in the solution. The Raman intensity levels are plotted against 4-ATP concentration in FIG. 6B indicating that the detection signal is enhanced by a magnetic concentration method that yields a very low detection limit of at least as low as 1 fM.

Figure 7:
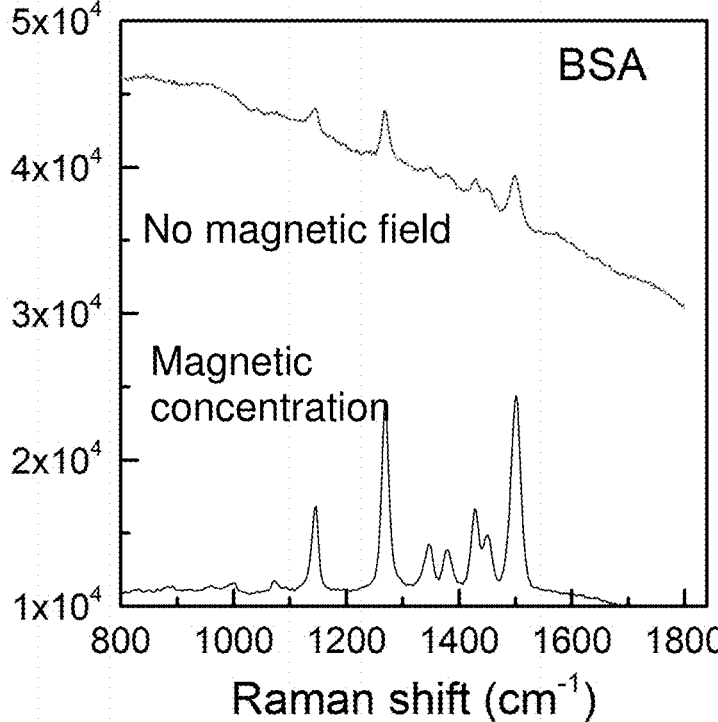
FIG. 7 provides Raman spectra of bovine serum albumin (BSA) with one embodiment of a silver nanoparticle associated with magnetic nanoparticles according to the present invention, both with and without magnetic concentration, illustrating the increased Raman signal that is obtained by probe concentration.

Such enhanced Raman spectrum measurements can be further applied to analyze low-concentration proteins. That is, magnetic concentration of the probes significantly increases the intensity (a.u.) of signals in the Raman spectra. FIG. 7, for example, shows the enhanced Raman intensity of bovine serum albumin (BSA) detected by using magnetic nanoparticle decorated silver nanoparticle probes under magnetic concentration.

Example 5

This example describes an immunodetection process, which can be used, for example, for early diagnosis of a cytokine storm. Some exemplary embodiments of the disclosed sensing technology take advantage of nanoparticles, such as silver nanoparticles in a core, associated with magnetic nanoparticle(s) and antibody on the core surface for high-speed capture of target molecules. The captured target is labeled to enhance sensing signals using a Raman-encoded biofunctional nanoparticle (RNP) that comprises a metal nanoparticle, such as silver and gold nanoparticles, associated with both Raman reporters and target receptors, such as molecularly imprinted polymer and secondary antibody, on the particle surface. The Raman reporter can be 4-mercaptobenzoic acid (MBA), 5,5'-dithio-bis(2-nitro-benzoic acid) (DTNB), and 2,3,5,6-tetrafluoro-4-mercaptobenzoic acid (TFMBA) to produce distinguishable Raman signals at 1075, 1334, and 1630 $cm^{-1}$, respectively. The magnetic concentration of the probes, along with the Raman-encoded nanoparticles, enables ultrasensitive, rapid-detection of multiple cytokines simultaneously from blood samples. The assay is made in a way that the detection signal from the Raman reporter or fluorescence reporter is enhanced by the strong local electric field on the metal nanoparticles excited by illumination. After the target molecule is captured by the MNP@NP probe and RNP reporter, an enhanced Raman signal can be detected.

In alternative embodiments, the RNP Raman reporter can be replaced by a fluorescence reporter. If the RNP Raman reporter is replaced by a fluorescence reporter, after the target molecule is captured by the MNP@NP probe and the reporter, an enhanced fluorescence signal can be detected. The probes are concentrated on a substrate by a magnetic field to further enhance the detection signal and reduce the background noise. This detection method can be used, for example, to detect low trace amounts of cytokines early to enable precise profiling of infections of SARS-COV-2, the virus that causes COVID-19.

Early diagnosis of cytokine storm in COVID-19 patients will allow prompt initiation of immunomodulatory treatment. There is an urgent need for a novel onsite diagnosis platform for rapid and sensitive detection of increasing trace amounts of inflammatory cytokines, wherein the amount can be as low as 25 pg/ml, including interleukin-6 (IL-6), IL-2, and IL-1B, in sputum or blood, as this analysis has great significance for early and precise profiling of the SARS-COV-2 infections. The method can also be applied to diagnosis of inflammation induced by other disease.

Disclosed embodiments of the present invention could replace conventional laboratory-based enzyme-linked immunosorbent assay (ELISA). The magnetic concentration of the probes and the RNP reporter labeling enables ultrasensitive, rapid detection of multiple cytokines simultaneously from blood samples. The detection procedure starts by capturing target cytokines using target-specific antibody-functionalized MNP@NPs. The captured targets are then labeled using RNP reporters through secondary antibodies or molecularly imprinted polymer (MIP) coated on the particle surface for creating Raman signals directly proportional to the number of captured cytokines. After the binding reaction, an external magnetic field is applied to concentrate the nanoparticles to a surface for Raman signal measurements. The synergistic effect of the strong plasmonic hotspot in the dual-particle complex and magnetic field concentrations enables a strong Raman signal from the reporter, which can be easily measured by a low-cost Raman spectrometer. The integrated hybrid system realizes a high-performance onsite cytokine detection platform.

Figure 8:
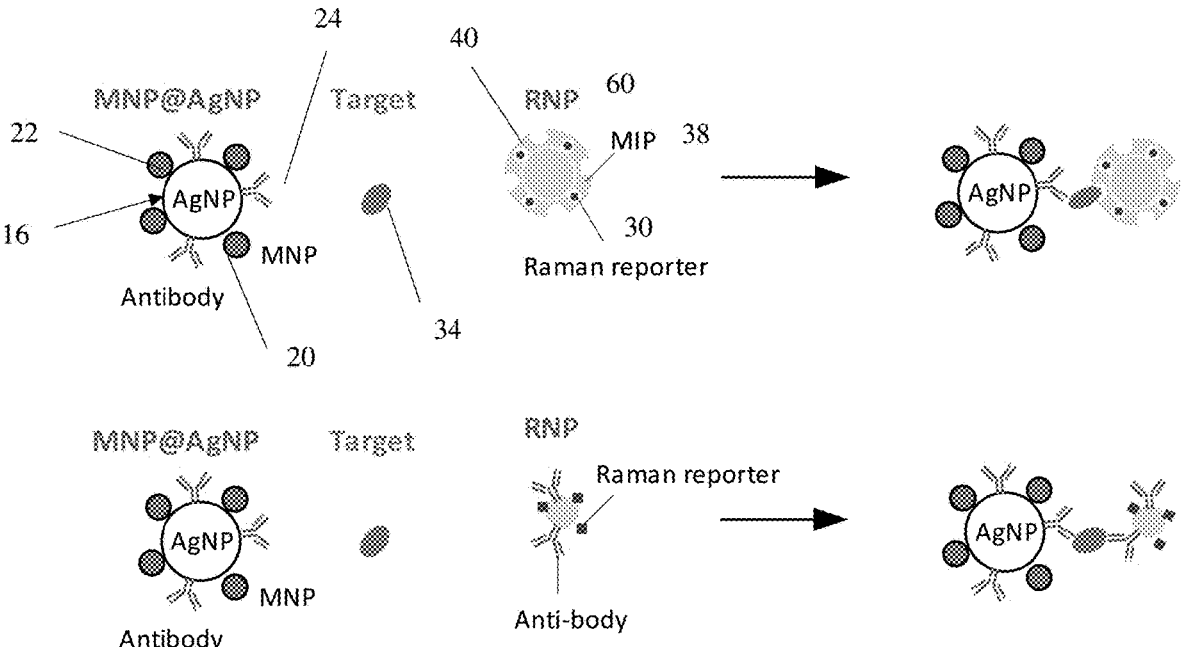
FIG. 8 is a schematic drawing illustrating a metal nanoparticle core comprising surface-associated magnetic nanoparticles interacting with a target and a reporter nanoparticle (RNP) comprising a molecularly imprinted polymer (MIP).

One embodiment of this method is illustrated by FIG. 8. FIG. 8 illustrates a composite structure 16 according to the present disclosure comprising a core nanoparticle 20, such as a silver nanoparticle, at least one, and typically plural magnetic nanoparticles 22, and at least one, and typically plural, biorecognition receptors 24, such as antibody, associated with the metal nanoparticle core. The antibody 24 recognizes a specific binding partner 34, such as a cytokine, as a target. Composite structure 16 binds to the target 34. Reporter 30 comprises a reporter nanoparticle 60 as a core with at least a portion of the reporter nanoparticle surface being associated with a molecularly imprinted polymer 38. Molecularly imprinted polymer 38 includes target recognition pockets 40 that also selectively recognize the target. Once bound, a composite structure 62 is formed that can be concentrated using an applied magnetic field, and concentrated structures 62 then detected using Raman spectroscopy.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A biosensor probe, comprising:

a core comprising a metal nanoparticle having a metal nanoparticle surface, the metal nanoparticle comprising a metal selected from gold, silver, copper, aluminum, and alloys thereof;

at least one magnetic nanoparticle associated with the core, the magnetic nanoparticle comprising iron, iron oxide, nickel, cobalt, or a combination thereof; and at least one reporter molecule.

2. The probe according to claim 1, comprising a plurality of magnetic nanoparticles associated with the metal nanoparticle core, the plurality of magnetic nanoparticles covering greater than 0 to less than 50% of the metal nanoparticle core surface.

3. The probe according to claim 2, wherein the plurality of magnetic nanoparticles covers from 10% to 30% of the metal nanoparticle core surface.

4. The probe according to claim 1, further comprising at least one recognition receptor associated with the metal nanoparticle for recognizing a selected target.

5. The probe according to claim 4, wherein the recognition receptor is a peptide, a protein, a nucleic acid, a molecularly imprinted polymer, or any combination thereof.

6. The probe according to claim 4, wherein the recognition receptor is an antibody.

7. The probe according to claim 4, wherein the recognition receptor is single or double stranded RNA or DNA.

8. The probe according to claim 4, wherein the reporter molecule is associated with the recognition receptor.

9. The probe according to claim 1, wherein the reporter molecule is selected from a fluorescent tag, a Raman reporter, or a combination thereof.

10. The probe according to claim 9, wherein the reporter molecule is a fluorescent dye and the metal nanoparticle size is selected to create a plasmon resonance spectrum that matches the light excitation or dye emission wavelength of the fluorescent dye to thereby enhance the fluorescence or Raman signal of the fluorescent dye.

11. The probe according to claim 1, wherein the metal nanoparticle size is varied, a percentage of the metal nanoparticle surface that is covered by magnetic particles is varied, or both are varied, to reduce or eliminate unwanted scattering or absorption of light contributed by the MNP.

12. A biosensor probe, comprising:

a core comprising a metal nanoparticle having a metal nanoparticle surface, the metal nanoparticle comprising a metal selected from gold, silver, copper, aluminum, and alloys thereof;

a plurality of magnetic nanoparticles associated with the core, the plurality of magnetic nanoparticles comprising iron, iron oxide, nickel, cobalt, or a combination thereof, and wherein the the plurality of magnetic nanoparticles covers greater than 0 to less than 50% of the metal nanoparticle core surface;

at least one recognition receptor associated with the metal nanoparticle for recognizing a selected target; and at least one reporter molecule associated with the metal nanoparticle, wherein the reporter molecule is a fluorescent tag, a Raman reporter, or a combination thereof.

13. A method, comprising:

providing a probe according to claim 1;

contacting a sample comprising a target of interest with the probe to form a probe-target composite;

concentrating probe-target composites using an applied magnetic field to form concentrated probe-target composites; and detecting the concentrated probe-target composites.

14. The method according to claim 13, wherein a plurality of probes are concentrated on a surface.

15. The method according to claim 13, wherein concentrating the probe-target composites enhances a sensing signal from 5 to 10 times compared to detection without concentrating the probes.

16. The method according to claim 13, wherein the probes are concentrated on a surface comprising an anti-fouling agent selected from bovine serum albumin, casein, an alkylene glycol, zwitterionic molecules, and combinations thereof.

17. The method according to claim 13, wherein detecting comprises detecting a fluorescent signal, obtaining a Raman spectrum, or both.

18. The method according to claim 13, wherein the target is a virus.

19. The method according to claim 13, wherein the virus is SARS-COV-2 or a mutant strain thereof.

20. The method according to claim 13, comprising:

obtaining a sputum or blood sample from a subject; and detecting interleukin-6 (IL-6), interleukin-2 (IL-2), interleukin-1β (IL-1β), or combinations thereof, in the sample at concentrations at least as low as 25 pg/ml.

21. A method, comprising:

providing a biosensor probe according to claim 12;

contacting a sample comprising a target of interest with the biosensor probe to form a probe-target composite;

concentrating probe-target composites on a surface using an applied magnetic field to form concentrated probe-target composites, thereby enhancing a sensing signal from 5 to 10 times compared to detection without concentrating the probes, the surface comprising an anti-fouling agent selected from bovine serum albumin, casein, an alkylene glycol, zwitterionic molecules, and combinations thereof; and detecting a fluorescent signal, obtaining a Raman spectrum, or both, from the concentrated probe-target composites.

22. The biosensor probe of claim 12, wherein the reporter molecule is a fluorescent dye and wherein the metal nanoparticle has a size selected to create a plasmon resonance spectrum that matches the light excitation or dye emission wavelength of the fluorescent dye to thereby enhance fluorescence or Raman signal of the fluorescent dye.

* * * * *